United States Patent
Garrison

(10) Patent No.: US 9,192,421 B2
(45) Date of Patent: Nov. 24, 2015

(54) BLADE LOCKOUT MECHANISM FOR SURGICAL FORCEPS

(71) Applicant: Covidien LP, Mansfield, MA (US)

(72) Inventor: David M. Garrison, Longmont, CO (US)

(73) Assignee: Covidien LP, Mansfield, MA (US)

( * ) Notice: Subject to any disclaimer, the term of this patent is extended or adjusted under 35 U.S.C. 154(b) by 186 days.

(21) Appl. No.: 13/833,823

(22) Filed: Mar. 15, 2013

(65) Prior Publication Data

US 2014/0031821 A1     Jan. 30, 2014

Related U.S. Application Data

(60) Provisional application No. 61/674,957, filed on Jul. 24, 2012.

(51) Int. Cl.
| | |
|---|---|
| *A61B 17/285* | (2006.01) |
| *A61B 18/08* | (2006.01) |
| *A61B 17/28* | (2006.01) |
| *A61B 18/14* | (2006.01) |

(52) U.S. Cl.
CPC ........... *A61B 18/085* (2013.01); *A61B 17/2833* (2013.01); *A61B 18/1442* (2013.01); *A61B 2018/1455* (2013.01)

(58) Field of Classification Search
CPC ........... A61B 18/1442; A61B 18/1445; A61B 18/1447; A61B 18/1455; A61B 18/1457; A61B 18/085; A61B 2018/1455; A61B 17/2833
USPC .................... 606/45, 49, 50, 51, 52
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Christopher D Koharski
*Assistant Examiner* — Michael Carey

(57) ABSTRACT

A forceps includes first and second shaft members and a trigger assembly. The first and second shaft members each have a jaw member disposed at a distal end thereof. One or both of the jaw members are moveable to position the jaw members between an open position and a closed position. One of the jaw members is configured for reciprocation of a blade therethrough. The trigger assembly is movable between unactuated and actuated positions to selectively translate the blade between a retracted position and one or more extended positions. The blade extends at least partially through one or both of the jaw members in the one or more extended positions such that when the blade is disposed in the one or more extended positions, the trigger assembly is configured to move to the unactuated position upon movement of the jaw members from the closed position to the open position.

18 Claims, 3 Drawing Sheets

(56) References Cited

U.S. PATENT DOCUMENTS

| | | |
|---|---|---|
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| 5,827,279 A | 10/1998 | Hughett et al. |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,618 B2 | 8/2006 | Couture |
| 7,101,371 B2 | 9/2006 | Dycus |
| D531,311 S | 10/2006 | Guerra et al. |
| 7,131,970 B2 | 11/2006 | Moses |
| 7,131,971 B2 | 11/2006 | Dycus |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| 7,252,667 B2 | 8/2007 | Moses et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson |
| D627,462 S | 11/2010 | Kingsley |
| D628,289 S | 11/2010 | Romero |
| D628,290 S | 11/2010 | Romero |
| D630,324 S | 1/2011 | Reschke |
| 7,922,718 B2 | 4/2011 | Moses |
| D649,249 S | 11/2011 | Guerra |
| D649,643 S | 11/2011 | Allen, IV et al. |
| 8,070,748 B2 | 12/2011 | Hixson |
| 8,092,451 B2 | 1/2012 | Schechter |
| 8,112,871 B2 | 2/2012 | Brandt |
| 8,133,254 B2 | 3/2012 | Dumbauld |
| 8,162,965 B2 | 4/2012 | Reschke |
| 8,187,273 B2 | 5/2012 | Kerr |
| D661,394 S | 6/2012 | Romero et al. |
| 8,215,182 B2 | 7/2012 | Artale |
| 8,257,352 B2 | 9/2012 | Lawes |
| 8,266,783 B2 | 9/2012 | Brandt |
| 8,277,446 B2 | 10/2012 | Heard |
| 8,287,536 B2 | 10/2012 | Mueller |
| 8,292,067 B2 | 10/2012 | Chowaniec |
| 8,292,886 B2 | 10/2012 | Kerr |
| 8,298,233 B2 | 10/2012 | Mueller |
| 8,323,310 B2 | 12/2012 | Kingsley |
| 8,343,150 B2 | 1/2013 | Artale |
| 8,343,151 B2 | 1/2013 | Siebrecht |
| 8,348,948 B2 | 1/2013 | Bahney |
| 8,357,159 B2 | 1/2013 | Romero |
| 8,388,647 B2 | 3/2013 | Nau, Jr. |
| 8,409,246 B2 | 4/2013 | Kerr |
| 8,409,247 B2 | 4/2013 | Garrison |
| 8,425,511 B2 | 4/2013 | Olson |
| 8,430,876 B2 | 4/2013 | Kappus |
| 8,430,877 B2 | 4/2013 | Kerr |
| 8,439,911 B2 | 5/2013 | Mueller |
| 8,439,913 B2 | 5/2013 | Horner |
| 2003/0018332 A1 | 1/2003 | Schmaltz |
| 2005/0119655 A1* | 6/2005 | Moses ............... A61B 18/1442 606/51 |
| 2006/0074417 A1 | 4/2006 | Cunningham |
| 2007/0088356 A1 | 4/2007 | Moses |
| 2007/0179499 A1* | 8/2007 | Garrison ........................ 606/51 |
| 2008/0300613 A1 | 12/2008 | Shelton, IV |
| 2009/0012520 A1 | 1/2009 | Hixson |
| 2010/0063500 A1* | 3/2010 | Muszala ........................ 606/48 |
| 2010/0204697 A1 | 8/2010 | Dumbauld |
| 2010/0204698 A1 | 8/2010 | Chapman |
| 2010/0217258 A1 | 8/2010 | Floume |
| 2010/0249769 A1 | 9/2010 | Nau, Jr. |
| 2010/0249776 A1 | 9/2010 | Kerr |
| 2010/0274244 A1 | 10/2010 | Heard |
| 2010/0280511 A1 | 11/2010 | Rachlin |
| 2010/0331839 A1 | 12/2010 | Schechter |
| 2011/0004210 A1 | 1/2011 | Johnson |
| 2011/0034918 A1 | 2/2011 | Reschke |
| 2011/0046623 A1 | 2/2011 | Reschke |
| 2011/0054468 A1* | 3/2011 | Dycus ........................ 606/45 |
| 2011/0054471 A1 | 3/2011 | Gerhardt |
| 2011/0060334 A1 | 3/2011 | Brandt |
| 2011/0060335 A1 | 3/2011 | Harper |
| 2011/0071523 A1 | 3/2011 | Dickhans |
| 2011/0073594 A1 | 3/2011 | Bonn |
| 2011/0077648 A1 | 3/2011 | Lee |
| 2011/0082494 A1 | 4/2011 | Kerr |
| 2011/0118736 A1 | 5/2011 | Harper |
| 2011/0184405 A1 | 7/2011 | Mueller |
| 2011/0190653 A1 | 8/2011 | Harper |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin |
| 2011/0238067 A1 | 9/2011 | Moses |
| 2011/0251605 A1 | 10/2011 | Hoarau |
| 2011/0251606 A1 | 10/2011 | Kerr |
| 2011/0251611 A1 | 10/2011 | Horner |
| 2011/0270245 A1 | 11/2011 | Horner |
| 2011/0270250 A1 | 11/2011 | Horner |
| 2011/0270251 A1 | 11/2011 | Horner |
| 2011/0276048 A1 | 11/2011 | Kerr |
| 2011/0276049 A1 | 11/2011 | Gerhardt |
| 2011/0295251 A1 | 12/2011 | Garrison |
| 2011/0295313 A1 | 12/2011 | Kerr |
| 2011/0301599 A1 | 12/2011 | Roy |
| 2011/0301600 A1 | 12/2011 | Garrison |
| 2011/0301602 A1 | 12/2011 | Roy |
| 2011/0301603 A1 | 12/2011 | Kerr |
| 2011/0301604 A1 | 12/2011 | Horner |
| 2011/0301605 A1 | 12/2011 | Horner |
| 2011/0301606 A1 | 12/2011 | Kerr |
| 2011/0319886 A1 | 12/2011 | Chojin |
| 2011/0319888 A1 | 12/2011 | Mueller |
| 2012/0010614 A1 | 1/2012 | Couture |
| 2012/0022532 A1 | 1/2012 | Garrison |
| 2012/0029515 A1 | 2/2012 | Couture |
| 2012/0041438 A1 | 2/2012 | Nau, Jr. |
| 2012/0046660 A1 | 2/2012 | Nau, Jr. |
| 2012/0046662 A1 | 2/2012 | Gilbert |

(56) References Cited

U.S. PATENT DOCUMENTS

| | | |
|---|---|---|
| 2012/0059371 A1 | 3/2012 | Anderson |
| 2012/0059372 A1 | 3/2012 | Johnson |
| 2012/0059374 A1 | 3/2012 | Johnson |
| 2012/0059375 A1 | 3/2012 | Couture |
| 2012/0059408 A1 | 3/2012 | Mueller |
| 2012/0059409 A1 | 3/2012 | Reschke |
| 2012/0083785 A1 | 4/2012 | Roy |
| 2012/0083786 A1 | 4/2012 | Artale |
| 2012/0083827 A1 | 4/2012 | Artale |
| 2013/0103030 A1 | 4/2013 | Garrison |
| 2013/0103031 A1 | 4/2013 | Garrison |
| 2013/0103035 A1 | 4/2013 | Horner |
| 2013/0103041 A1 | 4/2013 | Regadas |
| 2013/0116690 A1 | 5/2013 | Unger |
| 2013/0123780 A1 | 5/2013 | Mckenna |
| 2013/0123837 A1 | 5/2013 | Roy |
| 2013/0131672 A1 | 5/2013 | Romero |
| 2013/0138101 A1 | 5/2013 | Kerr |
| 2013/0138102 A1 | 5/2013 | Twomey |
| 2013/0138104 A1 | 5/2013 | Romero |
| 2013/0138129 A1 | 5/2013 | Garrison |
| 2013/0144284 A1 | 6/2013 | Behnke, II |
| 2013/0150842 A1 | 6/2013 | Nau, Jr. |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026 179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 1532932 | 5/2005 |
| EP | 1609430 | 12/2005 |
| EP | 1810625 | 7/2007 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/045589 | 6/2002 |
| WO | WO 2005/110264 | 11/2005 |
| WO | WO 2006/021269 | 3/2006 |
| WO | WO 2008/040483 | 4/2008 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/741,550, filed Jan. 15, 2013, Deborski.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.

(56) References Cited

OTHER PUBLICATIONS

U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/853,259, filed Mar. 29, 2013, Garrison.
U.S. Appl. No. 13/853,273, filed Mar. 29, 2013, Kerr.
U.S. Appl. No. 13/853,339, filed Mar. 29, 2013, Reschke.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

* cited by examiner

BLADE LOCKOUT MECHANISM FOR SURGICAL FORCEPS

CROSS REFERENCE TO RELATED APPLICATION

The present application claims the benefit of and priority to U.S. Provisional Application Ser. No. 61/674,957, filed on Jul. 24, 2012, the entire contents of which are incorporated herein by reference.

BACKGROUND

The present disclosure relates to surgical forceps and, more particularly, to blade lockout mechanisms for use in surgical forceps for sealing and dividing tissue.

TECHNICAL FIELD

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

SUMMARY

According to one aspect, a forceps includes first and second shaft members and a trigger assembly. Each of the first and second shaft members has a jaw member disposed at a distal end thereof. One or both of the jaw members is moveable to position the jaw members between an open position and a closed position for grasping tissue between the jaw members. One or both of the jaw members is adapted to connect to a source of electrosurgical energy. The forceps may include an actuator for controlling the supply of electrosurgical energy to one or both jaw members. A tab may be secured to one of the first and second shaft members and the actuator may be secured to the other of the first and second shaft members. Upon the application of a pre-determined closure force to one or both of the first and second shaft members, the tab engages the actuator to supply electrosurgical energy to one or both jaw members. One or both of the jaw members is configured for reciprocation of a blade therethrough.

The trigger assembly is movable between an unactuated position and an actuated position to selectively translate the blade between a retracted position and one or more extended positions. The blade extends at least partially through one or both of the jaw members in the one or more extended positions such that when the blade is disposed in the one or more extended positions, the trigger assembly is configured to move to the unactuated position upon movement of the jaw members from the closed position to the open position. The blade is prevented from being disposed in the one or more extended positions when the jaw members are disposed in the open position.

The trigger assembly includes a trigger and one or more linkages. The one or more linkages are coupled at a first end to the trigger and coupled at a second end to the blade. Movement of the trigger drives the one or more linkages to translate the blade between the retracted position and the one or more extended positions. The trigger is secured to one of the first and second shafts via a pivot pin that enables the trigger to rotate as the trigger assembly moves between the actuated and unactuated positions. The trigger includes a first camming surface and one of the first and second shaft members includes a second camming surface. When the first and second camming surfaces are engaged, movement of the trigger is limited. The trigger may be laterally disposed on one of the first and second shaft members wherein at least a portion of the trigger may be substantially aligned with at least a portion of the other of the first and second shaft members in a plane parallel to a longitudinal axis defined through the forceps. This facilitates engagement between the first and second camming surfaces upon approximating movement between the trigger and the other of the first and second shaft members.

In another aspect, a forceps includes first and second shaft members, a blade, and a trigger. The first and second shaft members each have a jaw member disposed at a distal end thereof. One or both of the jaw members are moveable to position the jaw members between an open position and a closed position for grasping tissue between the jaw members. One or both of the jaw members are adapted to connect to a source of electrosurgical energy. The forceps may include an actuator for controlling the supply of electrosurgical energy to one or both of the jaw members. The forceps may include an actuator for controlling the supply of electrosurgical energy to one or both jaw members. A tab may be secured to one of the first and second shaft members and the actuator may be secured to the other of the first and second shaft members. Upon the application of a pre-determined closure force to one or both of the first and second shaft members, the tab engages the actuator to supply electrosurgical energy to one or both jaw members.

The blade is configured for reciprocation through one or both of the jaw members. The trigger is movable between an unactuated position and an actuated position to selectively translate the blade between a retracted position and one or more extended positions. The blade is prevented from being disposed in the one or more extended positions when the jaw members are disposed in the open position.

The trigger may be secured to one of the first and second shafts via a pivot pin that enables the trigger to rotate between the actuated and unactuated positions. The trigger is prevented from being disposed in the actuated position when the jaw members are disposed in the open position. Jaw opening movement of one of the first and second shaft members biases the trigger to the unactuated position to retract the blade toward the retracted position when the blade is disposed in the one or more extended positions. The trigger includes a first camming surface and one of the first and second shaft members includes a second camming surface. When the first and second camming surfaces are engaged, movement of the trigger is limited. The trigger may be laterally disposed on one of the first and second shaft members wherein at least a portion of the trigger may be substantially aligned with at least a portion of the other of the first and second shaft members in a plane parallel to a longitudinal axis defined through the forceps. This facilitates engagement between the first and second camming surfaces upon approximating movement between the trigger and the other of the first and second shaft members.

The forceps may include one or more linkages. The one or more linkages are coupled at a first end to the trigger and coupled at a second end to the blade. Movement of the trigger drives the one or more linkages to translate the blade between the retracted position and the one or more extended positions.

BRIEF DESCRIPTION OF THE DRAWINGS

Various embodiments of the subject forceps are described herein with reference to the drawings wherein.

DETAILED DESCRIPTION

Figure 1:
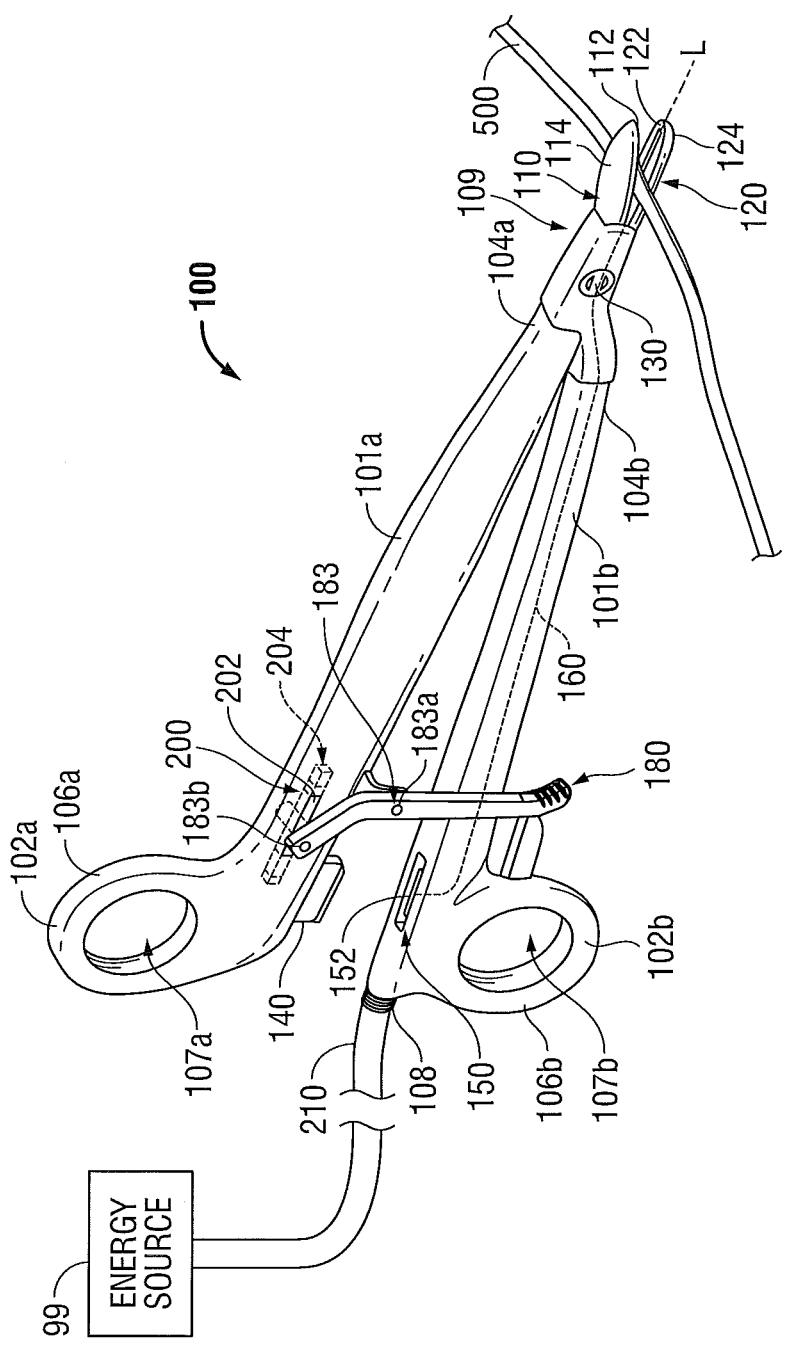
FIG. 1 is a side, perspective view of a forceps according to an embodiment of the present disclosure.

Referring initially to FIG. 1, a forceps 100 includes two elongated shaft members 101a, 101b each having a proximal end 102a, 102b and a distal end 104a, 104b, respectively. In the drawings and in the descriptions which follow, the term "proximal," as is traditional, will refer to the end of forceps 100 that is closer to the user, while the term "distal" will refer to the end that is further from the user.

Forceps 100 includes an end effector assembly 109 attached to distal ends 104a, 104b of shaft members 101a, 101b, respectively. As explained in more detail below, end effector assembly 109 includes a pair of opposing jaw members 110, 120 that are pivotably connected about a pivot pin 130.

Figure 6:
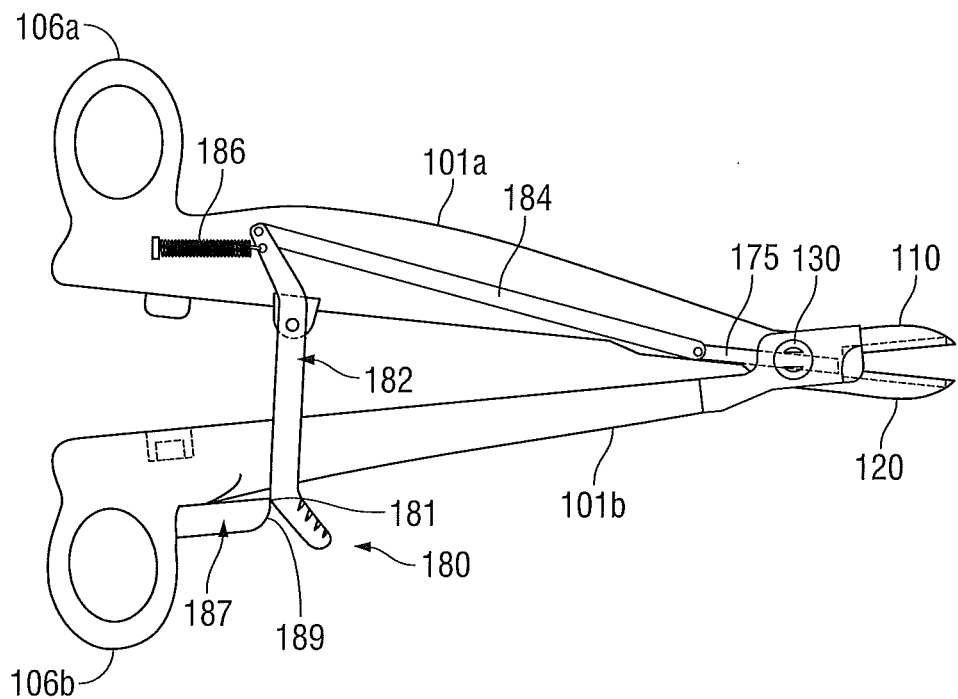

Each shaft member 101a, 101b includes a handle 106a, 106b disposed at proximal end 102a, 102b, respectively, thereof. Each handle 106a, 106b defines a finger hole 107a, 107b, respectively, therethrough for receiving a finger of the user. Finger holes 107a, 107b facilitate movement of shaft members 101a, 101b relative to one another which, in turn, pivots jaw members 110, 120 from an open position (FIGS. 1 and 6), wherein jaw members 110, 120 are disposed in spaced-apart relation relative to one another to a closed position (FIGS. 3 and 4), wherein jaw members 110, 120 cooperate to grasp tissue 500 therebetween. With brief reference to FIG. 3, a projecting member 187 may extend from one or more of shaft members 101a, 101b and/or handles 106a, 106b.

With continued reference to FIG. 1, one of the shafts, e.g., shaft member 101b, includes a proximal shaft connector 108 that connects forceps 100 to an internal or external energy source 99 such as an electrosurgical generator or other suitable power source. Proximal shaft connector 108 secures an electrosurgical cable 210 to forceps 100 such that the user may selectively apply electrosurgical energy from the energy source 99 to either (or both) of jaw members 110, 120 as needed.

As mentioned above, opposing jaw members 110 and 120 of end effector assembly 109 are pivotable about pivot pin 130 from the open position to the closed position for grasping tissue 500 therebetween. Jaw member 110 includes an outer housing 114 that is configured to mechanically engage an electrically conductive sealing surface 112 of jaw member 110. Similarly, jaw member 120 includes an outer housing 124 that is configured to mechanically engage an electrically conductive sealing surface 122 of jaw member 120. Outer housings 114 and 124 may be insulated but need not be insulated as long as sealing surface 112 of jaw member 110 is isolated from sealing surface 122 of jaw member 120 Electrically conductive sealing surfaces 112 and 122 are opposed to one another, such that, upon activation, electrosurgical energy may be supplied to the electrically conductive sealing surfaces 112 and 122 for sealing tissue 500 disposed between jaw members 110 and 120. More particularly, a first electrical potential may be provided to first jaw member 110 and a second electrical potential may be provided to second jaw member 120 to conduct energy between sealing surfaces 112, 122 of jaw members 110, 120, respectively, to seal tissue 500 disposed therebetween.

A tab 140 disposed at proximal end 102a of shaft member 101a extends from shaft member 101a toward shaft member 101b. A corresponding recess 150 is defined within shaft member 101b toward proximal end 102b thereof and is configured to receive tab 140 therein. Upon approximation of shaft members 101a, 101b, e.g., when jaw members 110, 120 are moved to the closed position, tab 140 enters recess 150 (see FIG. 3). Upon further approximation of shaft members 101a, 101b, e.g., upon application of a pre-determined closure force to jaw members 110, 120, tab 140 is advanced further into recess 150 to depress actuator 152 disposed therein (see FIG. 4). Actuator 152 controls the supply of electrosurgical energy to jaw members 110, 120 such that, upon depression of actuator 152, electrosurgical energy is supplied to sealing surface 112 and/or sealing surface 122 of jaw members 110, 120, respectively, to seal tissue 500 grasped therebetween. More particularly, actuator 152 may be in electrical communication with jaw members 110, 120 via an electrical communication link 160 (e.g., a cable or any other suitable connection known in the art) (see FIG. 1). Other more standardized activation switches are also contemplated, e.g., finger switch, toggle switch, foot switch, etc.

Figure 2:
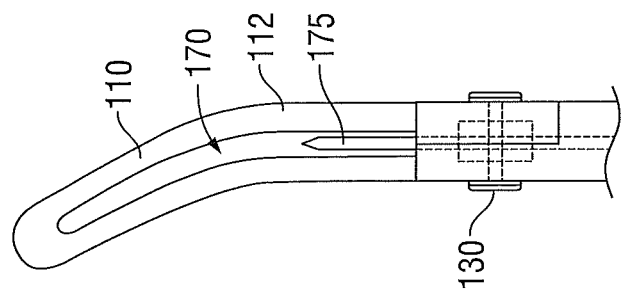
FIG. 2 is a top view of a jaw member of the forceps of FIG. 1.

As best seen in FIG. 2, jaw member 110 includes a blade slot, or blade channel 170 extending therethrough. Blade channel 170 is configured for reciprocation of a cutting mechanism, e.g., a blade 175, therethrough. As shown, blade channel 170 is defined completely within jaw member 110. However, blade channel 170 may be formed when two opposing blade channels defined within jaw members 110, 120 come together upon pivoting of jaw members 110, 120 to the closed position. Further, blade channel 170 may be configured to facilitate and/or enhance cutting of tissue during reciprocation of cutting blade 175 in the distal direction.

Figure 3:
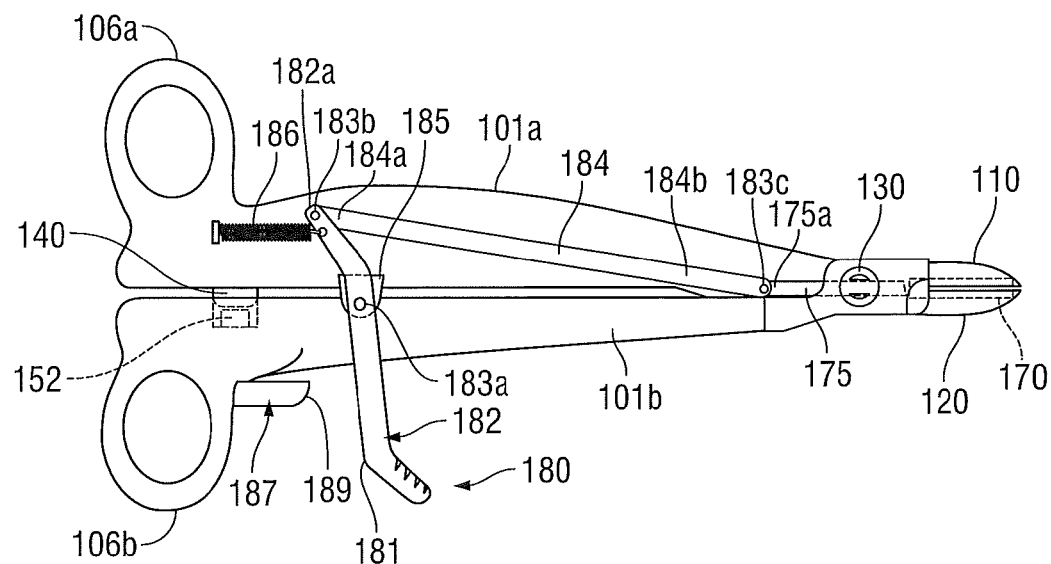
FIGS. 3-6 are progressive side views of the forceps of FIG. 1 illustrating various positions of a trigger assembly and jaw members thereof, where a portion of the handle has been removed to show the internal components therein.

Referring now to FIGS. 1 and 3, shaft member 101a of forceps 100 includes a trigger assembly 180. Trigger assembly 180 includes one or more rotatable triggers 182, one or more biasing members 186 (e.g., springs), one or more linkages 184, and one or more pivot pins 183. Notably, linkage 184 may be a flexible member (e.g., spring steel, plastic, or other suitable material) or a guided member (e.g., wire or metal ribbon), in which case, pivot pin 183 may be a living hinge or a rigid connector. Trigger 182 is pivotably coupled to shaft member 101a (or shaft member 101b as long as projecting member 187 is attached to the opposite shaft member) via one or more pivot pins 183. More particularly, trigger 182 may be laterally disposed on one of first and second shaft members 101a, 101b and pivotably secured thereto by one or more pivot pins 183. Pivot pin 183a may be secured to an extension 185 to pivotably mount trigger 182 to one of first and second shaft members 101a, 101b. Extension 185 may project from shaft member 101a or shaft member 101b. A proximal end 184a of linkage 184 is secured to a top portion 182a of trigger 182 via pivot pin 183b. Biasing member 186 is secured to proximal end 184a of linkage 184 and/or top portion 182a of trigger 182. A distal end 184b of linkage 184 is pivotably coupled to blade 175 at a proximal end 175a of blade 175 via pivot pin 183c.

As trigger assembly 180 moves from an unactuated position to an actuated position, trigger 182 rotates to advance blade 175 from shaft member 101a into blade channel 170 to divide tissue 500 grasped between jaw members 110, 120. In this manner, rotation of trigger 182 effects longitudinal translation of blade 175. When trigger 182 is in the unactuated position (FIG. 3), blade 175 is retracted within shaft member 101a. Conversely, when trigger 182 is disposed in one of the actuated positions (see FIGS. 4-5) blade 175 extends at least partially through blade channel 170. As will be described in greater detail below, advancement of blade 175 through blade channel 170 may be inhibited when jaw members 110, 120 are in the open position (see FIGS. 1, 5 and 6). As further described below, trigger 182 may be biased toward the unactuated position such that blade 175 is retracted within shaft member 101a when jaw members 110, 120 move towards the open position from a closed position.

With reference now to FIGS. 3-6, trigger assembly 180 is movable between the unactuated position and the actuated position to selectively translate blade 175 between a retracted position and one or more extended positions. More specifically, rotational movement of trigger 182 drives linkage 184 to translate blade 175 between retracted and extended positions. Notably, either or both shaft members 101a, 101b may have an arcuate or curvilinear configuration to accommodate vertical and/or movement of proximal end 184a of linkage 184 (see FIGS. 3-6) as trigger 182 moves linkage 184 between the retracted and extended positions.

As best depicted in FIG. 1, either or both shaft members 101a, 101b may define a slot 200 that may be linear, curvilinear or any other suitable shape to accommodate sliding movement of pivot pin 183b therethrough as trigger assembly 180 moves between the actuated and unactuated positions. Slot 200 accommodates pivot pin 183b to facilitate the axial and/or rotational movement of pivot pin 183b (see FIGS. 3-6). One or more shudders 202 may be seated in a track 204 formed in slot 200 on opposed sides of pivot pin 183b to prevent fluid from entering into one of shaft members 101a, 101b as trigger assembly 180 moves between the actuated and unactuated positions. Shudders 202 are configured to translate along slot 200 in track 204 in accordance with the movement of pivot pin 183b.

The slot arrangement may not necessarily be required. In alternative embodiments, trigger assembly 180 may include any suitable mechanical arrangement for facilitating movement of trigger assembly 180 relative to one or both of the shaft members 101a, 101b between the actuated and unactuated positions. For instance, linkage 184, or portions thereof, may be completely outside of either or both shaft members 101a, 101b. According to one example, trigger assembly 180 may include a coupling member (e.g., a ring, saddle, etc.) supported on an exterior surface of either or both shaft members 101a, 101b to facilitate movement of trigger assembly 180 between the actuated and unactuated positions as the coupling member, or portions thereof, moves along the exterior surface of the respective shaft member(s). Either or both shaft members 101a, 101b may be hollow to facilitate movement of trigger assembly 180, or portions thereof, through either or both shaft members 101a, 101b as trigger assembly 180 is moved between the actuated and unactuated positions.

In certain embodiments, pin 183a may not be required. For example, magnets may be positioned on each of linkage 184 and trigger 182 to facilitate movement of the trigger assembly 180 between actuated and unactuated positions. According to another example, linkage 184 and trigger 182 may be coupled together with a tether.

As will be described in detail below, trigger 182 is biased in the unactuated or "at-rest" position, by biasing member 186, whereby linkage 184 and blade 175 are biased in the retracted position, as shown in FIG. 3. In the unactuated position of trigger 182, jaw members 110, 120 are moveable between the open (unapproximated) position and the closed (approximated) position. When trigger 182 is unactuated, linkage 184 is retracted and disposed in a proximal-most position wherein blade 175 is disposed completely within shaft member 101a of forceps 100, or at least proximal to tissue engaging surfaces 112, 122 of jaw members 110, 120, respectively. When trigger 182 is actuated, linkage 184 and blade 175 extend, at least partially, between jaw members 110, 120.

Figure 4:
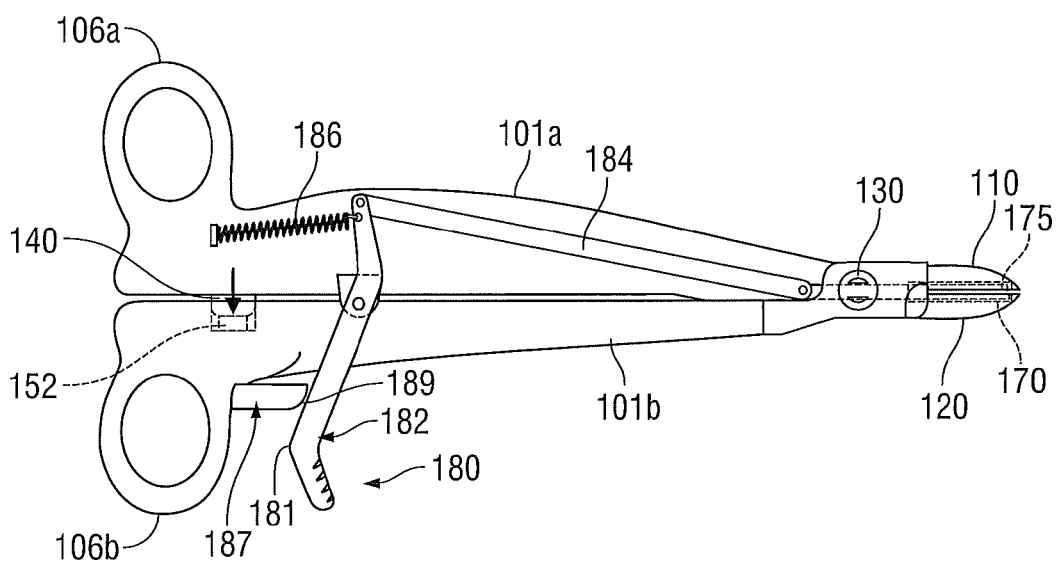

Referring again to FIG. 4, once electrosurgical energy has been conducted through tissue 500 (FIG. 1) grasped between sealing surfaces 112, 122 of jaw members 110, 120 to seal tissue 500 (or where it is desired to simply grasp and divide tissue), blade 175 may be advanced through blade channel 170 to cut tissue 500 grasped between jaw members 110, 120. More particularly, in order to advance blade 175 into channel 170, trigger 182 is rotated in a clockwise direction. Rotation of trigger 182 effects distal translation of linkage 184 against the bias of biasing member 186. The distal translation of linkage 184, in turn, effects distal translation of blade 175 from shaft member 101a into blade channel 170 (FIGS. 2 and 4). In this regard, rotation of trigger 182 advances linkage 184 distally such that blade 175 is advanced into blade channel 170 defined within jaw member 110 to cut tissue 500 grasped between jaw members 110, 120.

Upon release of trigger 182, trigger 182 is rotated counterclockwise under the bias of biasing member 186 such that linkage 184 and blade 175 are returned proximally to the retracted position within shaft member 101a. Accordingly, trigger assembly 180 is configured such that blade 175 is automatically retracted after deployment through blade channel 170. At this point, with tissue 500 having been sealed and divided, and with blade 175 in the retracted position, jaw members 110, 120 may be moved to the open, or spaced-apart position, to release tissue 500 such that forceps 100 may be withdrawn from the surgical site.

Turning again to FIGS. 4-6, blade 175 extends at least partially through one or both of the jaw members 110, 120 in the one or more extended positions such that when blade 175 is disposed in the one or more extended positions, trigger assembly 180 is configured to move to the unactuated position upon movement of jaw members 110, 120 from the closed position to the open position (see FIG. 5). Likewise, blade 175 is prevented from being disposed in the one or more extended positions when jaw members 110, 120 are disposed in the open position (see FIGS. 1 and 6).

Figure 5:
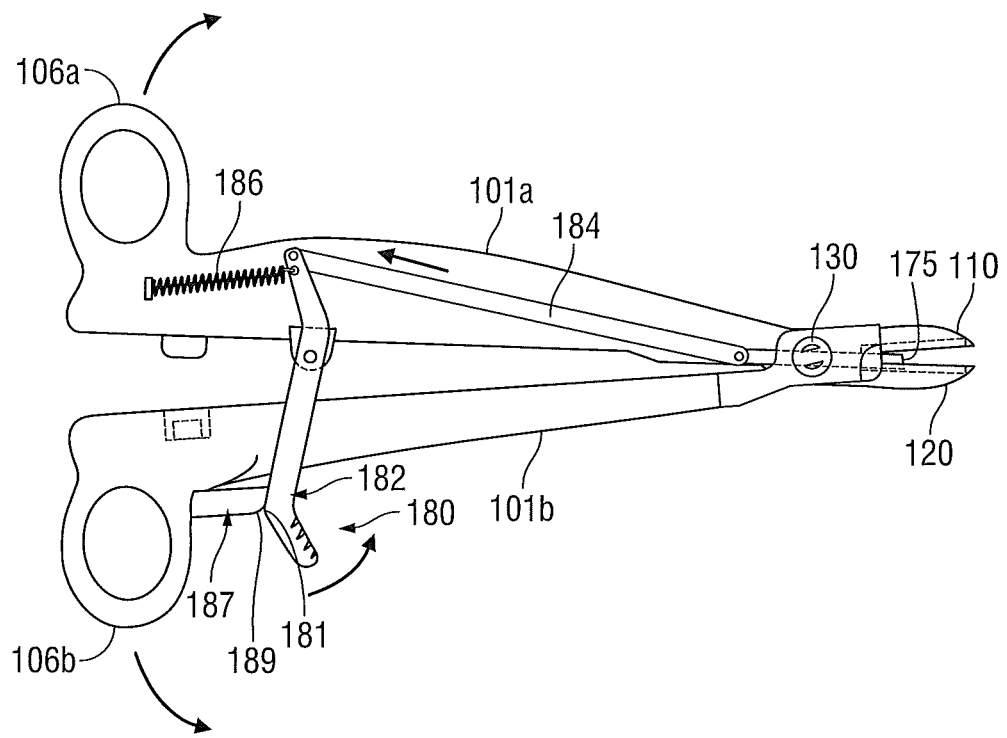

To this end, trigger 182 includes a first camming surface 181 (FIG. 3) while projecting member 187, which may extend from one or more of shaft members 101a, 101b and/or handles 106a, 106b (e.g., attached to the shaft and/or handle opposite the trigger 182) as discussed above, includes a second camming surface 189. Projecting member 187 and trigger 182 may be substantially aligned in a plane parallel to a longitudinal axis "L" (FIG. 1) defined through forceps 100 to facilitate contacting engagement of first and second camming surfaces 181, 189 upon approximating movement between the projecting member 187 and trigger 182 so that when first and second camming surfaces 181, 189 are engaged, movement of trigger 182 is limited. Notably, trigger 182 is prevented from being disposed in the actuated position when jaw members 101*a*, 101*b* are disposed in the open position as discussed above (see FIGS. 1 and 6). In particular, to open jaw members 110, 120, handles 106*a*, 106*b* and/or shaft members 101*a*, 101*b* unapproximate. Upon unapproximating handles 106*a*, 106*b* and/or shaft members 101*a*, 101*b* a predetermined amount, first and second camming surfaces 181, 189 become engaged, thereby locking trigger 182 in the unactuated position by preventing proximal actuation of trigger 182 to prevent deployment of blade 175. In similar regard, as best depicted in FIG. 5, when trigger 182 is disposed in the actuated position, jaw opening movement of shaft members 101*a*, 101*b* and/or handles 106*a*, 106*b* drives trigger 182 from the actuated position to the unactuated position to retract blade 175 toward the retracted position when blade 175 is disposed in the one or more extended positions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   first and second shaft members, each of the first and second shaft members having a handle disposed at a proximal end thereof and a jaw member disposed at a distal end thereof, the handles of the first and second shaft members movable relative to one another to pivot the first and second shaft members in relation to one another such that the jaw members move between an open position and a closed position for grasping tissue between the jaw members, at least one of the jaw embers configured for reciprocation of a blade therethrough; and
   a trigger assembly movable between an unactuated position and an actuated position to selectively translate the blade between a retracted position and at least one extended position, the blade extending at least partially through at least one of the jaw members in the at least one extended position such that when the blade is disposed in the at least one extended position, the trigger assembly is configured to move to the unactuated position upon movement of the jaw members from the closed position to the open position.

2. The forceps according to claim 1, wherein the trigger assembly includes a trigger and a least one linkage, the at least one linkage coupled at a first end to the trigger and coupled at a second end to the blade.

3. The forceps according to claim 2, wherein movement of the trigger drives the at least one linkage to translate the blade between the retracted position and the at least one extended position.

4. The forceps according to claim 2, wherein the trigger is secured to one of the first and second shaft embers via a pivot pin that enables the trigger to rotate as the trigger assembly move between the actuated and unactuated positions.

5. The forceps according to claim 2, wherein the trigger includes a first camming surface and one of the first and second shaft members includes a second camming surface, and wherein when the first and second camming surfaces are engaged, movement of the trigger is limited.

6. The forceps according to claim 5, wherein the trigger is laterally disposed on one of the first and second shaft members, and wherein at least a portion of the trigger is substantially aligned with at least a portion of the other of the first and second shaft members in a plane parallel to a longitudinal axis defined through the forceps to facilitate an engagement between the first and second camming surfaces upon approximating movement between the trigger and the other of the first and second shaft members.

7. The forceps according to claim 1, wherein the blade is prevented from being disposed in the at least one extended position when the jaw members are disposed in the open position.

8. The forceps according to claim 1, wherein at least one of the jaw members is adapted to connect to a source of electrosurgical energy, the forceps further comprising an actuator for controlling the supply of electrosurgical energy to at least one jaw member.

9. The forceps according to claim 8, wherein a tab is secured to one of the first and second shaft members and the actuator is secured to the other of the first and second shaft members, and wherein, upon the application of a pre-determined closure force to at least one of the first and second shaft members, the tab engages the actuator to supply electrosurgical energy to the at least one jaw member.

10. A forceps, comprising:
    first and second shaft members, each of the first and second shaft members having a handle disposed at a proximal end thereof and a jaw member disposed at a distal end thereof, the handles of the first and second shaft members movable relative to one another to pivot the first and second shaft members in relation to one another such that the jaw members move between an open position and a closed position for grasping tissue between the jaw members;
    a blade configured for reciprocation through at least one of the jaw members; and
    a trigger movable between an unactuated position and an actuated position to selectively translate the blade between a retracted position and at least one extended position, the trigger prevented from being disposed in the actuated position when the jaw members are disposed in the open position;
    wherein jaw opening of one of the first and second shaft members biases the trigger to the unactuated position to retract the blade toward the retracted position when the blade is disposed in the at least one extended position.

11. The forceps according to claim 10, further comprising at least one linkage, the at least one linkage coupled at a first end to the trigger and coupled at a second end to the blade.

12. The forceps according to claim 11, wherein movement of the trigger drives the at least one linkage to translate the blade between the retracted position and the at least one extended position.

13. The forceps according to claim 10, wherein the trigger is secured to one of the first and second shaft members via a pivot pin that enables the trigger to rotate between the actuated and unactuated positions.

14. The forceps according to claim 10, wherein the trigger includes a first camming surface and one of the first and second shaft members includes a second camming surface, and wherein when the first and second camming surfaces are engaged, movement of the trigger is limited.

15. The forceps according to claim 14, wherein the trigger is laterally disposed on one of the first and second shaft members, and wherein at least a portion of the trigger is substantially aligned with at least a portion of the other of the first and second shaft members in a plane parallel to a longitudinal axis defined through the forceps to facilitate an engagement between the first and second camming surfaces upon approximating movement between the trigger and the other of the first and second shaft members.

16. The forceps according to claim 10, wherein the blade is prevented from being disposed in the at least one extended position when the jaw members are disposed in the open position.

17. The forceps according to claim 10, wherein at least one of the jaw members is adapted to connect to a source of electrosurgical energy, the forceps further comprising an actuator for controlling the supply of electrosurgical energy to at least one jaw member.

18. The forceps according to claim 17, wherein a tab is secured to one of the first and second shaft members and the actuator is secured to the other of the first and second shaft members, and wherein, upon the application of a pre-determined closure force to at least one of the first and second shaft members, the tab engages the actuator to supply electrosurgical energy to the at least one jaw member.

* * * * *